United States Patent [19]
Sharpless et al.

[11] Patent Number: 5,859,281

[45] Date of Patent: Jan. 12, 1999

[54] CATALYTIC ASYMMETRIC AMINOHYDROXYLATION OF OLEFINS WITH SULFONAMIDES

[75] Inventors: K. Barry Sharpless; Guigen Li, both of La Jolla; Han-Ting Chang, San Diego, all of Calif.

[73] Assignee: The Scripps Research Institute, La Jolla, Calif.

[21] Appl. No.: 651,819

[22] Filed: May 21, 1996

[51] Int. Cl.[6] .................................................. C07C 303/00
[52] U.S. Cl. ................................................................ 560/12
[58] Field of Search .................................................. 560/12

[56] References Cited

PUBLICATIONS

Journal Of Amer. Chem. Soc., vol. 115, No. 18, pp. 8463–8464, Morikawa et al, 1993.

Primary Examiner—Samuel Barts
Attorney, Agent, or Firm—Donald G. Lewis

[57] ABSTRACT

β-Hydroxyamines and β-hydroxysulfonamides are synthesized from olefin substrates by means on a catalyzed asymmetric addition reaction. The addition reaction is catalyzed by osmium and is co-catalyzed by chiral ligands. The chiral ligands, in addition to being co-catalysts with the osmium, also serve to direct the addition reaction regioselectively and enantioselectively. Divalent ligands are preferred over monovalent ligands because of their enhance regio- and enantio-selectivity. Sulfonamides are employed as an oxidant nitrogen source for the production of β-hydroxysulfonamides. Excellent yields and enantiomeric efficiencies are achieved with co-solvents containing a 50/50 (v/v) mixtures of water and organic solvent. β-Hydroxyamines are obtained by deprotecting the corresponding β-hydroxysulfonamides.

8 Claims, 17 Drawing Sheets

| Substrate | Product | %ee (DHQ)₂-PHAL | Yield (%) | Time (h) |
|---|---|---|---|---|
| Ph‾‾‾‾CO₂Me | TsNH⋯S⋯R⋯CO₂Me / Ph / OH  2 | 82(89 [a]) | 60(51 [a]) | 3 |
| Ph‾‾‾‾Ph | TsNH⋯S⋯S⋯Ph / Ph / OH  7 | 64(99 [b]) | 78(50 [b]) | 3 |
| Ph‾‾‾‾Ph (cis) | TsNH⋯OH⋯S⋯Ph / R / Ph  8 | 50 | 57 | 2.5 |

Figure 6

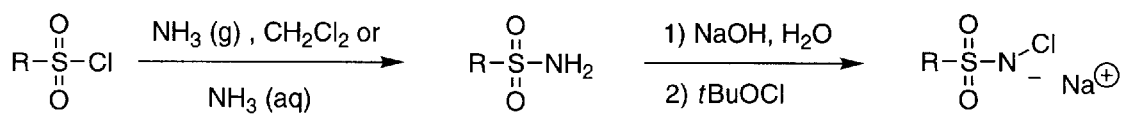

R = 4-Me-Ph-, 4-MeOPh, Me, Ph-CH$_2$- , 4-NO$_2$-Ph-, 2-NO$_2$-Ph-
2-Naphthyl,1-Napthyl, Dansyl or derivatives selected from the following functional groups: acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, CH$_n$X where X=OR$_1$, halogens, aromatic rings, heterocycles, silyl groups and n=1 to 2.

Figure 9

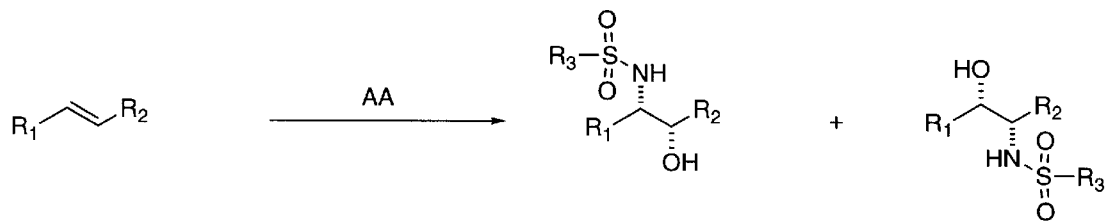

R₁ = acyclic or cyclic hydrocarbons, heterocycles, hydroxyl compounds, ethers, protected amines, sulfides, carbonyl compounds, acrylates, substituted acrylates, esters or carboxylic acids R₂ = combination of R₁

R₃ = 4-Me-Ph-, 4-MeOPh, Me, Ph-CH₂- , 4-NO₂-Ph-, 2-NO₂-Ph-
2-Naphthyl,1-Napthyl, Dansyl or derivatives selected from the following functional groups: acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, CH$_n$X where X=OR₁, halogens, aromatic rings, heterocycles, silyl groups and n=1 to 2.

Figure 10

R =  4-Me-Ph-
4-MeO-Ph-
Me-
Ph-CH2-
TMS-CH2-CH2-
4-NO2-Ph -
2-Naph.
1-Naph.
Dansyl

|  | R-SO$_2$-NH$_2$ | time [h] | %ee | regioselectivity | yield* [%] |
|---|---|---|---|---|---|
| 28:29 | 4-Me-Ph- | 2 | 66 | 80 : 20 | |
| 30:31 | 4-MeO-Ph- | 2 | 58 | 65 : 35 | |
| 32:33 | Me- | 4 | 80 | 83 : 17 | |
| 34:35 | Ph-CH$_2$- | 8 | 85 | 8 : 2 | 38 |
| 36:37 | TMS-CH$_2$-CH$_2$- | 2 | 70 | 83 : 17 | 48 |
| 38:39 | 4-NO$_2$-Ph- | 6 | 67 | 81 : 19 | |
| 40:41 | 2-NO$_2$-Ph- | 6 | 70 | 72 : 25 | |
| 42:43 | 2-Naph. | 3 | 79 | | 50 |
| 44:45 | 1-Naph. | 4 | 62 | 96 : 4 | |
| 46:47 | Dansyl | 5 | (50) | 96 : 4 | |

Figure 12

| Substrate | Product | %ee (DHQ)$_2$-PHAL | (DHQD)$_2$-PHAL | Yield$^2$(%) | Time (h) | m.p. (°C) | $[\alpha]_D^{25}$ [c] |
|---|---|---|---|---|---|---|---|
| Ph⌒CO$_2$CH$_3$ | MeSO$_2$NH–Ph–CO$_2$CH$_3$, OH  50 | (81) | (71) | (64) | | | |
| Ph⌒CO$_2$iPr | MeSO$_2$NH–Ph–CO$_2$iPr, OH  32 | (66) | 0 | 0 | | | |
| H$_3$CO$_2$C⌒CO$_2$CH$_3$ | MeSO$_2$NH–H$_3$CO$_2$C–CO$_2$CH$_3$, OH  49 | 95 (77) | 94 (53) | 63 (65) | | | |
| Ph⌒Ph | MeSO$_2$NH–Ph–Ph, OH  51 | 75 (62) | 82 (50) | 71 (51) | | | |
| H$_3$C⌒CO$_2$tBu | MeSO$_2$NH–H$_3$C–CO$_2$tBu, OH  52 | 80 | 82 | 63 | 16 | | |
| cyclohexene | MeSO$_2$NH, OH cyclohexane 53 | (45) | (36) | (64) | | 116-117 | |

Figure 15

AA of Acrylates and Methacrylates

| Entry | R | R' | ee [%] a |
|---|---|---|---|
| 1 | Me | H | 42 (38)* |
| 2 | Et | H | 46 |
| 3 | n-Hexyl | H | 47 |
| 4 | i-Bu | H | 40 (30)* |
| 5 | c-Hexyl | H | 49.5 |
| 6 | t-Bu | H | 56 (37)* |
| 7 | t-Bu | H | 70** (57)*** |
| 8 | Stearyl | H | - |
| 9 | Me | Me | 9 |
| 10 | t-Bu | Me | 32 (18)* |

AA of t-Butyl Acrylate

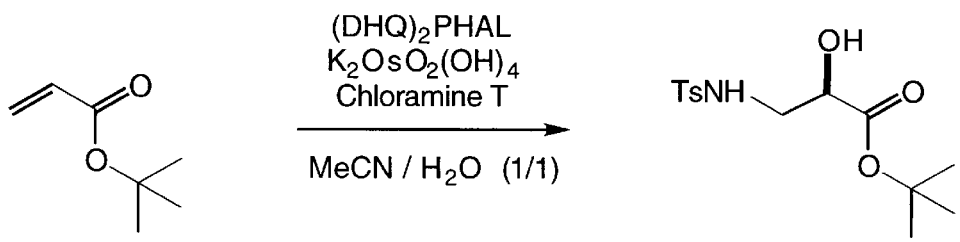

| | |
|---|---|
| Std. Conditions | 56 % ee, (54 %) |
| Std. Conditions + NaCl (heterogen.) | 54 % ee |
| Std. Conditions + 0 °C | 53 % ee |
| Std. Conditions + 1.5 eq. CT | 53 % ee |
| Std. Conditions + 4 % "Os" + 2 % Ligand | 50 % ee |
| Std. Conditions + tBuOH / H$_2$O | 56 % ee * |
| Std. Conditions + EtOH / H$_2$O | 16 % ee * |
| Std. Conditions + 0.5 % "Os" + 0.5 % Ligand | 42% ee |
| Std. Conditions + 0.8 % "Os" + 1 % (DHQ)$_2$-DPP Ligand | 59 % ee |
| Std. Conditions + (DHQ)$_2$-DPP Ligand | 70 % ee |

\* Low yield

Std. Conditions:

(DHQ)$_2$PHAL (5 %), K$_2$OsO$_2$(OH)$_4$ (4 %) Chloramine T (3 eq.)

Figure 17

CATALYTIC ASYMMETRIC AMINOHYDROXYLATION OF OLEFINS WITH SULFONAMIDES

FIELD OF INVENTION

The invention relates to the regio-selective and enantioselective conversion of olefins to β-hydroxyamines and β-hydroxysulfonamides. More particularly, the invention relates to catalytic asymmetric additions or aminohydroxylations of olefins and other unsaturated substrates using sulfonamide as an oxidizing agent in the presence of an osmium catalyst and a chiral ligand.

Background

The β-hydroxyamine group is a common motif found in biologically active molecules. For example, the C-13 side-chain of taxol includes a β-hydroxyamine group and is known to be essential for the biological activity of taxol. Hence synthesis of the side-chain and its analogs is a subject of significant recent interest. Modifications of the taxol side-chain are an important aspect of the structure-activity-relationship (SAR). Among numerous synthetic approaches, the asymmetric catalytic methods hold special interest. The catalytic asymmetric dihydroxylation (AD) and asymmetric epoxication (AE) have been successfully applied in syntheses of the C-13 side-chain. (Denis, J.-N., et al., Journal of Organic Chemistry, 51(1986) 46; Denis, J.-N., et al., Journal of Organic Chemistry, 55(1990) 1957; Deng, L. and Jacobsen, E. N. Journal of Organic Chemistry, 57(1992) 4320; and Wang, Z.-M., et al., Journal of Organic Chemistry, 59(1994)5104).

Sharpless et al. first demonstrated that β-hydroxysulfonamides could be obtained using either stoichiometric or catalytic amounts of 1% osmium tetraoxide in the presence of 1.5–5 equivalents of Chloramine-T trihydrate ($TsSO_2NClNa.3H_2O$, Ts=tosylate; commercially obtained) to effect cis addition of a hydroxyl (OH) and an arylsulfonamide moiety (Ar—$SO_2NH$) across a mono or disubstituted olefinic linkages (Sharpless et. al. *J. Org. Chemistry* 1976, 41, 177).

Two procedures were developed to effect hydroxyamination of olefins using sulfonamides. (Sharpless et al. *Org. Syn.* 1980, 61, 85). The first procedure used phase transfer catalysis conditions at 55°–60° C. with 1% $OsO_4$, 1:1 V/V, 0.20 Molar $CHCl_3/H_2O$, and benzyltriethylammonium chloride as the phase transfer catalyst. The chloramine T-trihydrate ($TsSO_2NClNa:3H_2O$) was either added directly or formed in situ in water; this solution was then directly used in the phase transfer mixture. The in situ procedure, for generating the chloramine salts, involved stirring a suspension of the arylsulfonamide with an equivalent of sodium hypochlorite (Clorox) until a homogenous solution was obtained. The yields were comparable with those obtained with isolated chloramine salts and the procedure was found most effective for monosubstituted and 1,2 disubstituted olefins. The phase transfer method, however, gave poor results with trisubstituted and 1,1-disubstituted olefins and the procedure did not succeed with diethyl fumarate and 2-cyclohexen-1-one. Sharpless et al. *J. Org. Chem.* 1978, 43, 2544.

A second procedure was carried out in tert-butyl alcohol at 55°–60° C. with 1% $OsO_4$, silver nitrate (with or without) and commercially obtained chloramine T-trihydrate ($TsSO_2NClNa.3H_2O$) which provided the only source of water. The procedure did not succeed with tetramethylethylene and cholesterol, and negative results were found with most hindered tri- and tetrasubstituted olefins. Sharpless et. al. *J. Org. Chemistry* 1976, 41, 177; Sharpless et al. *Org. Syn.* 1980, 61, 85. The addition of divalent metal salts such as $AgNO_3$ and $Hg(NO_3)_2$ improved some reactions, however, other reactions suffered deleterious effects from the addition of the metal salts. Sharpless et al. *J. Org Chem.* 1978, 43, 2544; Sharpless et. al. *J. Org. Chemistry* 1976, 41, 177.

Further elaboration on either procedure showed that other sulfonamide derivatives ($ArSO_2NClNa$) could be successfully employed in addition to chloramine T, where Ar=phenyl, o-tolyl, p-chlorophenyl, p-nitrophenyl, and o-carboalkoxyphenyl. Sharpless et al. *J. Org. Chem.* 1978, 43, 2546.

Neither the phase transfer catalyst or tert-butyl alcohol procedures succeeded with tetramethyl ethylene, 2,3-dimethyl-2-octene, diethyl fumarate, or 2-cyclohexen-1-one. Negative results were also obtained with most hindered tri- and tetrasubstituted olefins. Herranz E., MIT Ph.D. Thesis, 1979, 33.

Solvent conditions for the synthesis of the hydroxysulfonamides included organic solvents such as acetonitrile, tert-butyl alcohol, isopropyl alcohol and chloroform which was in contact with the aqueous phase in the phase transfer catalyst procedure.

The tert-butyl alcohol procedure (including other solvents used) was not run with added water; the phase transfer catalyst (PTC) procedure required a biphasic mixture of 1:1 v/v chloroform/water. Recently, however, an improvement was reported which used a 1:1 ratio of organic solvent to water in a homogeneous, rather than a biphasic solution or organic solvent with small amounts of water. These conditions were found to provide optimum enantioselectivity, regioselectively and improved yields from either the previously described t-butyl alcohol or PTC conditions. Sharpless et al. *Angew. Chemie Intl Ed.* 1996, 35, 451.

The use of chiral ligands with sulfonamides provides enantioselectivity and has been observed to both accelerate and decelerate the rate of catalysis. The hydroxysulfonamide process is a stereoselective cis process. The presence of ligands also has a dramatic effect on the regioselectivity. In a study with no ligand present with methyl cinnamate, the two regioisomers were present in a 2:1 ratio. With the addition of ligand, the ratio was improved to 5:1 or greater. Another positive effect of the ligand was its ability to suppress formation of diol by-product. *Angew. Chemie Intl Ed.* 1996, 35, 451.

Preferred ligands for use with sulfonamides have included the use of monovalent cinchona alkaloids or the bivalent phthalazine based, commercially available $(DHQ)_2PHAL$ and $(DHQD)_2PHAL$ alkaloids. Sharpless et al. *Angew. Chemie Intl Ed.* 1996, 35, 451.

Temperature conditions for the hydroxysulfonamide asymmetric aminohydroxylations have varied from 60° C. to 25° C. for reactions including sulfonamides, auxiliary salts, ligands, phase transfer catalysts and stoichiometric or catalytic osmium species, primarily in organic solvents with small amounts of water. Recently, it has been shown that temperature can been lowered to 0° C. while running the reaction, to obtain product by filtration; many hydroxysulfonamides tend to be highly crystalline.

Cleavage of the sulfonamides, to free aminoalcohols, have been accomplished via standard deprotection conditions including dissolving metals (Na, $NH_3$; Sharpless et al *J. Org. Chem* 1976, 41, 177) and HBr, acetic acid and phenol (Fukuyama et al. *Tetrahedron Lett.* in press).

What is needed is an improved method for catalyzing the symmetric aminohydroxylation of olefins, wherein the improvement enhances the yields, enantiomeric efficiency, and the regio-selectivity while reducing material and labor costs.

SUMMARY OF THE INVENTION

The invention is directed to an improved method for converting olefinic substrates to asymmetric β-hydroxysulfonamide products. The method of the invention employs an asymmetric addition reaction involving the asymmetric addition of a nitrogen source and a hydroxyl radical to the olefinic substrate. Enhanced yields, regioselectivity, and enantioselectivity may be may be achieved according to the method of the invention. The asymmetric addition reaction is carried out in a reaction solution which includes the olefinic substrate, an osmium catalyst, a chiral ligand for enantiomerically and regioselectively directing the asymmetric addition, and a nitrogen source. The olefinic substrate is present and soluble within the reaction solution in stoichiometric amounts. The osmium is present within the reaction solution in catalytic amounts. One aspect of the improvement is directed to the use of a sulfonamide as the nitrogen source for forming an asymmetric hydroxysulfonamide intermediate. Preferred sulfonamides include chloramine compounds. Preferred reaction solutions include co-solvent mixtures containing both an organic component and an aqueous compound. Preferred organic components include acetonitrile, tert-butanol, and n-propanol. In a preferred co-solute, each of the organic and aqueous components is approximately 50% on a volume basis. In a preferred mode, the asymmetric hydroxysulfonamide reaction occurs in the substantial absence of ancillary salts, including silver salts and mercury salts. After the hydroxysulfonamide intermediate is formed, the asymmetric hydroxylamine product may obtained by deprotecting the asymmetric hydroxysulfonamide intermediate for forming the asymmetric hydroxylamine product.

BRIEF DESCRIPTION OF FIGURES

FIG. 6 tabulates a series of products formed from catalytic asymmetric aminohydroxylation in 1:1 t-BuOH/$H_2O$ (procedure 2). [a] In this case, one half of the olefin was added at the beginning of the reaction and the rest was added in portions over 45 min starting one hour later. [b] The minor enantiomer is completely removed by two triturations with ethyl acetate which leaves a 50% yield of enantiopure (S,S)-5.

FIG. 9 illustrates a general synthesis of N-chloro-N-sodio-R-sulfonamides $RSO_2NClNa$, where R consists of one of the following groups: 4-Me-Ph-, 4-MeOPh, Me, Ph-CH2-, 4-NO2-Ph-, 2-NO2-Ph-, 2-Naphthyl,1-Napthyl, Dansyl or derivatives selected from the following functional groups: acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, $CH_nX$ where $X=OR_1$, halogens, aromatic rings, heterocycles, silyl groups and n=1 to 2.

FIG. 10 illustrates a general aminohydroxylation reaction (AA) for the olefin $R_1CHCHR_2$ using N-chloro-N-sodio-$R_3$-sulfonamides $R_3SO_2NClNa$ and various reaction conditions including $K_2OsO_2(OH)_4$, 2–4%; $(DHQ)_2$-PHAL or $(DHQD)_2$-PHAL, 2.5–5%; $TsNClNa.3H_2O$, 3–5 eq.; indicated solvent mixes including $CH_3CN/H_2O$, n-propanol/$H_2O$, t-BuOH/$H_2O$, v/v=1:1 or (EtOH(5)/n-propanol(3)/$H_2O$ (5); room temp., 3–5 h, 0.01–0.07M in olefin.

R₁=acyclic or cyclic hydrocarbons, heterocycles, hydroxyl compounds, ethers, protected amines, sulfides, carbonyl compounds, acrylates, substituted acrylates, esters or carboxylic acids.

R₂=combination of R₁

R₃=4-Me-Ph-, 4-MeOPh, Me, Ph-CH2-, 4-NO2-Ph-, 2-NO2-Ph-, 2-Naphthyl,1-Napthyl, Dansyl or derivatives selected from the following functional groups:acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, CHnX where X=OR₁, halogens, aromatic rings, heterocycles, silyl groups and n=1 to 2.

Figure 11:
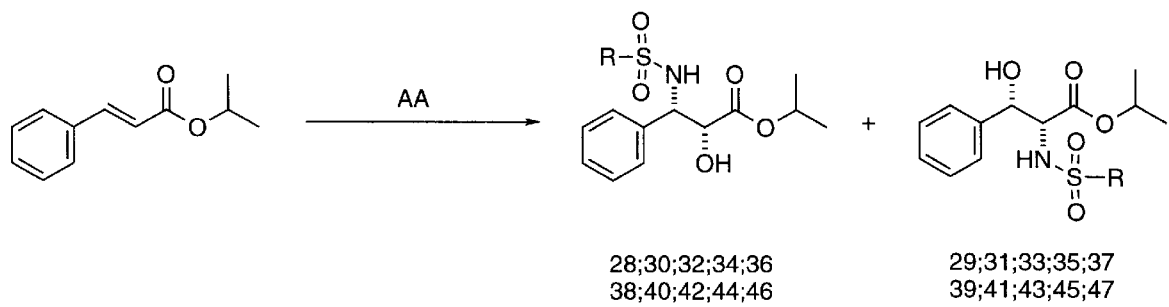

FIG. 11 illustrates the catalytic asymmetric aminohydroxylation of isopropyl cinnamate by addition of N-chloro-N-sodio-R-sulfonamides or in situ generation of R-SO₂NClNa via R-SO₂Cl. R=4-Me-Ph-, 4-MeOPh, Me, Ph-CH2-, 4-NO2-Ph-, 2-NO2-Ph, 2-Naphthyl,1-Napthyl, Dansyl or derivatives selected from the following functional groups:acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, CHnX where X=OR₁, halogens, aromatic rings, heterocycles, silyl groups and n=1 to 2.

FIG. 12 tabulates the catalytic asymmetric aminohydroxylation of isopropyl cinnamate by in situ generation of R-SO₂NClNa via R-SO₂NH₂ to give compounds 28–47 with respective conditions indicated. R=4-Me-Ph-, 4-MeOPh, Me, Ph-CH2-, 4-NO2-Ph-, 2-NO2-Ph, 2-Naphthyl,1-Napthyl, Dansyl or derivatives selected from the following functional groups:acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, CHnX where X=OR₁, halogens, aromatic rings, heterocycles, silyl groups and n=1 to 2.

Figure 13:
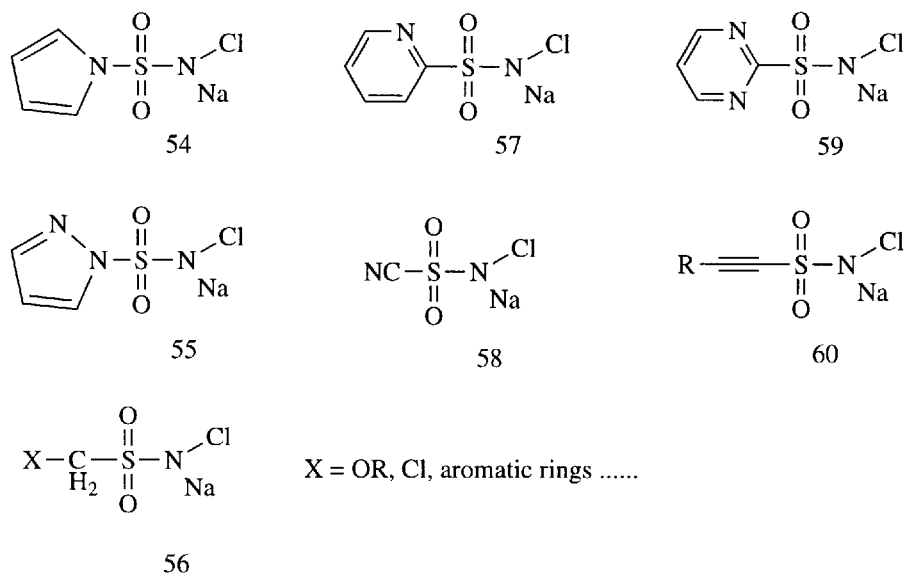

FIG. 13 illustrates additional N-chloro-N-sodio-R-sulfonamides derivatives R-SO₂NClNa selected from the following functional groups: R=acyclic or cyclic hydrocarbons, hydroxyl compounds, ethers, protected amines, carbonyl compounds, esters or carboxylic acids, n-alkyl, alkynes (60) pyrans, pyrroles (54), various heterocycles including: nitriles (58), pyrazines, pyrazoles (55), pyridazines, pyridines (57),pyrimidines (59), pyrrolizines, quinazolines, quionlines, thiophenes, silanes, CHnX where X=OR₁, halogens, aromatic rings, heterocycles, silyl groups and n=1 to 2 (56).

Figure 14:
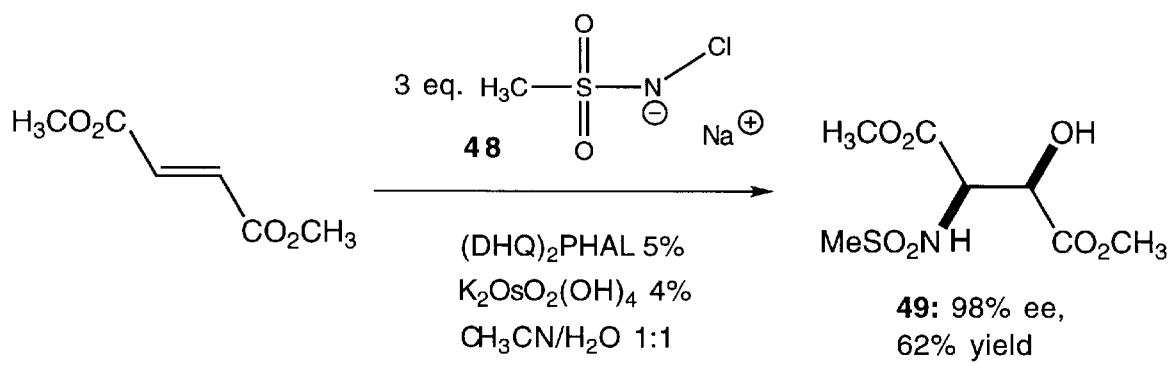

FIG. 14 illustrates the AA (asymetric aminohydroxylation) reaction of dimethylfumarate under conditions which utilize 3.0 equivalents of N-chloro-N-sodio-methanesulfonamide (Chloramine M) to achieve a 98% ee (enantiomeric excess) and 62% overall yield of 49.

FIG. 15 tabulates the AA (asymetric aminohydroxylation) for a series of substrates under conditions which utilize 3.0 equivalents of N-chloro-N-sodio-methanesulfonamide (Chloramine M). (1) performing this reaction at 17° C., the enantioselectivity was >98%; (2) yields not optimized.

Figure 16:
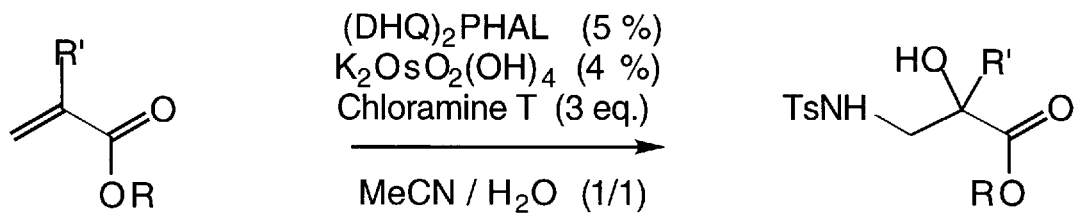

FIG. 16 illustrates a series of products formed from the AA (asymetric aminohydroxylation) of selected acrylates and methacrylates (entries 1–10). The synthetic conditions are as follows: K₂OsO₂(OH)₄, 4%; (DHQ)₂-PHAL or (DHQD)₂-PHAL, 5%; TsNClNa.3H₂O (chloramine T), 3 eq.; CH₃CN/H₂O or t-BuOH/H₂O, v/v=1:1; Room temp., 3 h, 0.07M in olefin.

FIG. 17 illustrates a series of products formed from the AA (asymmetric aminohydroxylation) of t-butyl acrylate. The synthetic conditions are as follows: K₂OsO₂(OH)₄, 4%; (DHQ)₂-PHAL or (DHQD)₂-PHAL, 5%; TsNClNa.3H₂O (chloramine T), 3 eq.; CH₃CN/H₂O or t-BuOH/H₂O, v/v= 1:1; Room temp., 3 h, 0.07M in olefin and indicated changes as noted with the respective enantiomeric excess (ee) listed.

DETAILED DESCRIPTION

A synthetic method is disclosed herein for obtaining β-hydroxysulfonamides and β-hydroxyamines directly from olefins in enantiomerically enriched form. The new osmium-catalyzed asymmetric process is exemplified in Scheme 1 by the synthesis of the Taxol sidechain enantiomers (2 and ent-2) from methyl cinnamate (1). This catalytic aminohydroxylation (AA) is obviously a close relative of the catalytic asymmetric dihydroxylation (AD), see H. C. Kolb, et al., Chem. Reviews 1994, 94, 2483. In fact, its stoichiometric analog was first reported in 1980 as a footnote in the initial report on the stoichiometric asymmetric dihydroxylation process, e.g., see note 22 in S. G. Hentges and K. B. Sharpless, J. Am. Chem. Soc. 1980, 102, 4263. Stoichiometric AA's have also been reported recently by H. Rubinstein and J. S. Svendsen, Acta Chem. Scand. 1994, 48, 439 and by C. Y. Park, Ph.D. thesis, Massachusetts Institute of Technology, Cambridge, Mass., 1991. However, both the AD and the AA, being at first only stoichiometric reactions, were pushed aside by the titanium-catalyzed asymmetric epoxidation process (AE), also discovered in 1980. (T. Katsuki and K. B. Sharpless, J. Am. Chem. Soc. 1980, 102, 5974.) Ever since the discovery of the catalytic AD in 1987, we have tried to render the AA catalytic. (E. N. Jacobsen, et al., J. Am. Chem. Soc. 1988, 110, 1968.) Initally, success was very limited. The first, albeit inefficient, asymmetric aminohydroxylations were performed by Christopher J. Burns and Declan Gilheanny in the Sharpless' laboratory at the Massachusetts Institute of Technology in 1987, unpublished results. It is disclosed herein how to run the reaction under conditions which allow the catalytic cycle to turnover at a useful rate. The process disclosed herein combines the AD's phthalazine ligands and the osmium-catalyzed aminohydroxylations. (See K. B. Sharpless, et al., Org. Chem. 1976, 41, 177; E. Herranz, et al., J. Org. Chem. 1978, 43, 2544; E. Herranz, et al., J. Am. Chem. Soc. 1978, 100, 3596; E. Herranz and K. B. Sharpless, J. Org. Chem. 1980, 45, 2710; E. Herranz and K. B. Sharpless, Org. Synth. 1983, 61, 85; E. Herranz and K. B. Sharpless, Org. Synth. 1981, 61, 93; For Palladium-promoted aminohydroxylation (oxyamination) see: J. E. Backvall and E. E. Bjorkman, J. Org. Chem. 1980, 43, 2893; and J. E. Backvall, Tetrahedron Lett. 1975, 26, 2225.) Other than the asymmetric induction, the most dramatic effect of the alkaloid ligand is on the regioselectivity. In the original study (no ligand present) with methyl cinnamate (1) the C-3 sulfonamide isomer 2 and its regioisomer, with the sulfonamide substituent at C-2, were produced in a 2:1 ratio. In the present system this ratio is improved to 5:1 or greater. In fact, at the early stage (i.e. ~5% conversion) of the reaction with methyl cinnamate this ratio is >20:1 and the enantiomeric purity of the major regioisomer (2) is about 95% ee. Both regioselectivity and enantioselectivity drop continuously as the reaction proceeds. This is tentatively attributed to intrusion of a "second cycle". Ethyl crotonate benefits from this same ligand effect. Another positive effect of the ligand is its ability to suppress formation of the diol by-product, which in the absence of the ligand is substantial in this new system.

Scheme 1: $K_2OsO_2(OH)_4$, 4%; $(DHQ)_2$-PHAL or $(DHQD)_2$-PHAL, 5%; TsNClNa.3H$_2$O, 3 eq.; CH3CN/H2O or t-BuOH/H2O, v/v = 1:1; Room temp., 3 h, 0.07M in olefin.

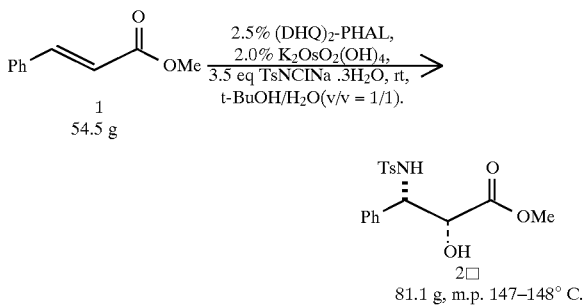

Legend for Scheme 1:
Catalytic asymmetric aminohydroxylation in 1:1 CH3CN/H2O (procedure 1).
[a] All absolute configurations have been determined, see experimental procedure.
[b] Numbers in parentheses are after recrystallizations from methanol (in some cases, [7] it is the mother liquor which is enantioenriched when the racemate crystallizes preferentially); the melting points and optical rotations (in 95% ethanol) are for the highest ee samples in the (DHQ)2-PHAL column.
[c] The ee's in this column are for the products which are enantiomeric to those in the "Product" column.
[d] 4:3 CH3CN/H2O was used as the solvent.

Scheme 1 reveals that the process in its present form yields only modest enantioselectivities (33–81%). On the other hand, the first report on the catalytic AD did not look much better (20–88% ee) [1a] and this new process offers considerably more variables for optimization efforts. Even the present results are useful since hydroxysulfonamides tend to be highly crystalline, and can usually be raised to enatiopurity by recrystallization. This is the case for the Taxol side-chain derivative 2, which following deprotection by treatment with 33% HBr in acetic acid for 10 hours at 75 EC gives the enantiopure α-hydroxy-β-amino acid in 70% yield. While the core functionality of toluenesulfonamide derivative 2 survives these strongly acidic conditions, many molecules would not. Indeed, the notorious problems associated with deprotection of sulfonamides are a serious concern for this AA process. Fortunately, there has been a breakthrough from the Fukuyama group (T. Fukuyama, et al., Tetrahedron Lett. 1995, 36, 6376.), which promises to make sulfonamide protection for nitrogen extremely popular. In any case, the vigorously acidic, yet successful conditions for deprotection of the Taxol side-chain precursor (vide supra) reveal that more molecules than previously imagined may tolerate the old brute-force approach for hydrolysis of aromatic sulfonamides.

Synthetic Protacals

General experimental. All reagents and solvents were purchased from commercial sources and used as received unless stated otherwise. All commercial chemicals were used without purification and their stoichiometries were calculated based on the reported purities from the manufacturer. (DHQD)$_2$PHAL,95% (hydroquinidine 1,4-phthalazinediyl diether), (DHQ)$_2$PHAL, 97% (hydroquinine 1,4-phthalazinediyl diether), chloramine-T-hydrate 98% (N-chloro-p-toluenesulfonamide, sodium salt) are commercially available from Aldrich Chemical Company. Additionally, the (DHQ)$_2$ and (DHQD)$_2$ ligands can be prepared from the procedure of Sharpless et al. J. Org. Chem. 1992, 57, 2768. Melting points were measured without correction with a Thomas-Hoover capillary apparatus. Optical rotations were recorded on an Autopol III polarimeter (Rudolph Research, Fairfield, N.J.). $^1$H and $^{13}$C NMR spectra were recorded on a Bruker AMX 400 instrument. Stoichiometries are calculated based on the purities reported by the manufacturer (trans-stilbene: 96%; Chloramine-T trihydrate: 98%). The $K_2OsO_2(OH)_4$ should be mauve rather than brown/black and should be dry for the best yields and ee's (the hygroscopic nature of the salt affects the amount of osmium dispensed). All new compounds gave satisfactory spectroscopic analyses ($^1$H-NMR, IR, HRMS). Enantiomeric excesses (ee's) were determined by HPLC using Chiracel columns (Daicel Chemical Industries) and isopropanol/hexane (v/v) mobile phases; the retention time of the major enantiomer from the (DHQ)$_2$-PHAL reaction is in italics. The vicinal hydroxysulfonamides derived from AA reactions using (DHQ)$_2$-PHAL as the chiral ligand were correlated to compounds of known absolute configuration by HPLC.

Figure 1:
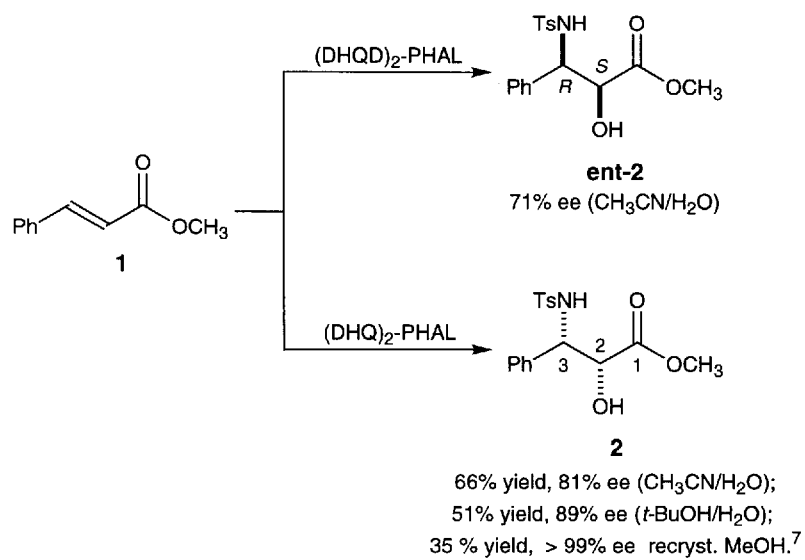
FIG. 1 illustrates the synthesis of α-hydroxy-β-sulfonamide compounds 2 and ent-2. The synthetic conditions are as follows: $K_2OsO_2(OH)_4$, 4%; $(DHQ)_2$-PHAL or $(DHQD)_2$-PHAL, 5%; $TsNClNa.3H_2O$, 3 eq.; $CH_3CN/H_2O$ or t-BuOH/$H_2O$, v/v=1:1; Room temp., 3 h, 0.07M in olefin.
Figure 2:
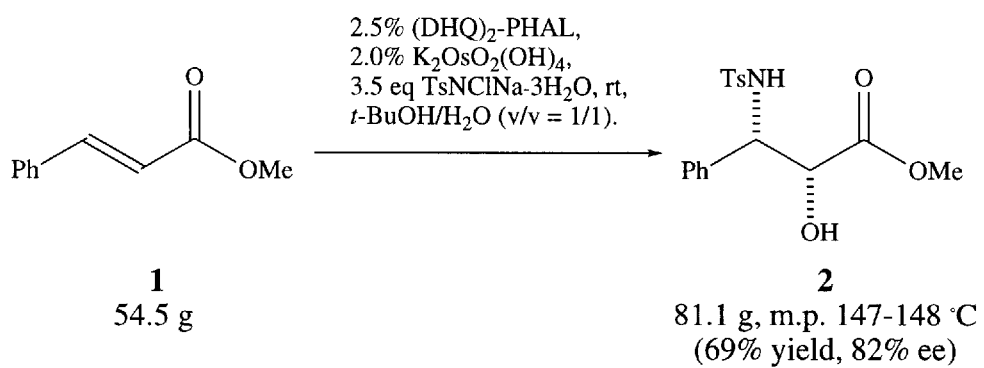
FIG. 2 illustrates the synthesis of α-hydroxy-β-sulfonamide compounds 2 in 1:1 v/v tBuOH/$H_2O$ and represents a solution-to-solid catalytic AA using only 2.5 mol % ligand and 2.0 mol % osmium catalyst. Product 2 crystallizes as it is formed, isolation includes only filtration of the crude mixture. The synthetic conditions are as follows: Methyl cinnamate 1, $K_2OsO_2(OH)_4$, 2.0%; $(DHQ)_2$-PHAL, 2.5%; $TsNClNa.3H_2O$, 3.5 eq.; tBuOH/$H_2O$, v/v=1:1; Room temp., 3 h, 0.07M in olefin; 69% yield, 82% ee.

Synthesis of (2R,3S)-(+)-Methyl-N-(p-toluenesulfonyl)-2-hydroxy-3-amino-3-phenyl-propionate (2) in t-BuOH (FIGS. 1 and 2)

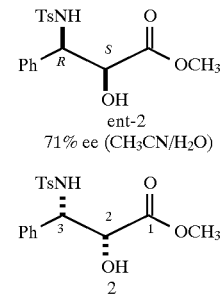

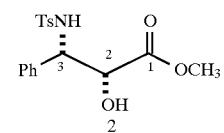

Compound 2. To a 2 L round-bottom flask, equipped with a mechanical stirrer and a thermometer, was added (DHQ)-PHAL (6.6 g, 2.5 mol %), t-BuOH (600 mL) and H$_2$O (600 mL). The flask was immersed in a room temperature water bath. To the resulting homogeneous solution was added in order 290.4 g (1.01 mol) of Chloramine-T trihydrate (ca. 4/5 of the total added which is in 338 g, 1.18 mol), methyl cinnamate (27.2 g, 167.6 mmol, half of the total amount of olefin, which is 54.4 g, 0.33 mol; Aldrich chemical company) and potassium osmate(VI; Aldrich) (2.5 g, 2.0 mol %). As the reaction was stirred, the color changed from yellow to green in 15 min and then back to yellow after 90 min; TLC(EtOAc/Hexane, v/v=4/6) revealed that the disappearance of olefin coincided with the return of the yellow color. The flask was then immersed in an ice bath (0° C.) for 20 min. (During this cooling, the crystals of precipitated product made their first appearance.) To this cold, stirred suspension the remainder of the Chloramine-T trihydrate (48.4 g, 0.168 mol) and the second portion of methyl cinnamate (13.6 g, 84 mmol) was added. The ice bath was replaced by the room temperature water bath, and the new olefin charge was consumed in about 45 min during which time the color changed as before from yellow to green and back to yellow again. The resulting mixture was cooled back to 0° C. for over 15 min and the third and last portion of methyl cinnamate (13.6 g, 84 mmol) was added. The reaction was returned to the room-temperature water bath and the remaining olefin was consumed in about 45 min with the above noted sequence of color changes. The flask was again immersed in an ice bath (0° C.) for about 20 min. Essentially all of the product precipitated out of solution and was isolated by filtration, washed twice with cold (ca 0° C.) 100 mL portions of t-BuOH/H$_2$O (v/v=1/1) to yield 81.1 g of (2R,3S)-(+)-methyl-N-(p-toluenesulfonyl)-2-hydroxy-3-amino-3-phenyl propionate (2) (69% yield, 82% ee, m.p. 147°–148° C.; for racemic: m.p. 125°–126° C. 4c).

A 6.3 g portion of this crude 2 was triturated with EtOAc at room temperature (1×75 mL, 1×35 mL and 2×20 mL), the solid triturand of 2 remaining after these triturations is of low ee and is discarded. Concentration of the combined triturates afforded 5.3 g of enantiomerically enriched 2 (58% yield, 92% ee), three recrystallizations from MeOH gave 3.2 g of enantiomerically pure product 2 (35% yield based on 1), m.p. 154°–155° C.; [a]\o(25,D)=+19.80 (c 0.5, 95% EtOH); $^1$H NMR (400 MHz, DMSO/D$_2$O) δ2.23 (s, 3H), 3.45 (s, 3H), 4.17 (d, J=4.0 Hz, 1H), 4.65 (d, J=4.0 Hz, 1H), 7.08–7.19 (m, 8H), 7.40 (d, J=8.2 Hz, 2H); $^{13}$C NMR (100 MHz, DMSO) δ 171.8, 141.9, 138.4, 138.7, 128.9, 127.6, 127.3, 126.9, 126.4, 74.4, 60.1, 51.6, 20.9.

Synthesis of (2R, 3S)-(+)-Methyl-N-(p-toluenesulfonyl)-2-hydroxy-3-amino-3-phenyl-propionate (2) in n-propanol:

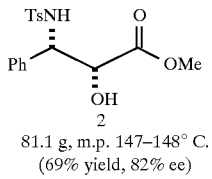

2
81.1 g, m.p. 147–148° C.
(69% yield, 82% ee)

To a solution of (DHQ)$_2$-PHAL (2.20 g, 2.80 mmol, 5 mol %) in n-Propanol (100 mL) and water (100 ml) in 500 mL Erlenmeyer or round-bottomed flask were added in order, methyl cinnamate (9.08 g, 56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 3 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/H$_2$O (15 mL) to yield 11.7 g of (2R,3S)-(+)-methyl-N-(p-toluenesulfonyl)-2-hydroxy-3-amino-3-phenyl propionate (60% yield, 89% ee).

Figure 3:
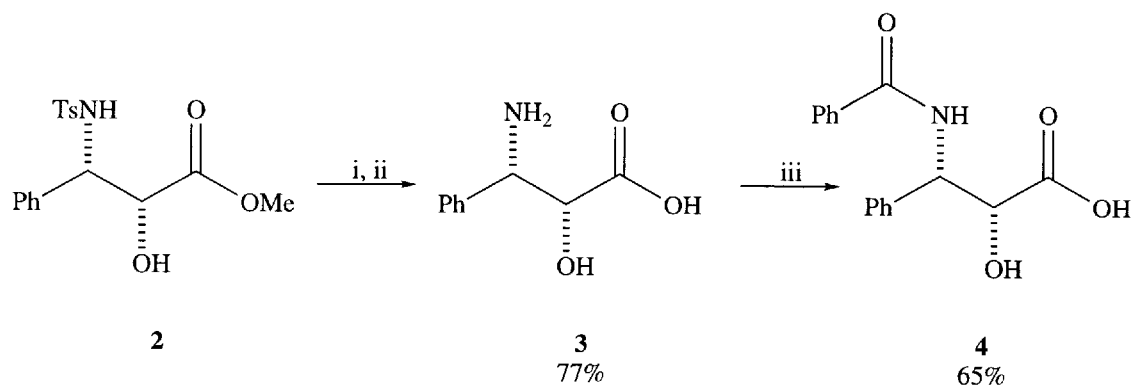
FIG. 3 illustrates the removal of the sulfonamide and methyl ester protecting groups from substrate 2 to form intermediate 3 which is subsequently converted to the taxol side chain via amide formation (step iii). The synthetic conditions are as follows: (i) HBr-HOAc, phenol, 75° C.; (ii) Amberlite 120 resin; (iii) PhCOCl, 2N NaOH, $H_2O$.

Synthesis of (2R, 3S)-2-hydroxy-3-amino-3-phenylpropionic acid (3); (FIG. 3)

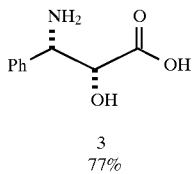

3
77%

Compound 3. A heavy-walled borosilicate pressure bottle was charged with the enantiomerically enriched (92% ee) 2 [i.e. the triturated but not recrystallized material (vide supra)] (1.25 g, 3.6 mmol), phenol (1.04 g, 11.1 mmol) and excess 33% hydrogen bromide in acetic acid (20 mL, 0.117 mol, Acros). The bottle was sealed with a bushing, having a Teflon-lined cap, before being immersed completely in an oil bath. The bath was maintained at 75° C. for 10–12 h. The resulting solution was then concentrated in vacuo to about 10 mL (water pump followed by an oil pump which was protected by a 0° C. aqueous KOH bubbler). The crude solution was purified by ion-exchange chromatography (Amberlite IR-120 resin, 35 g), elueting with 80 mL of water (to remove impurities), then with 80 mL of 10% ammonium hydroxide (start with a dilute solution due the heat generated in the ion exchange process) followed by 80 mL of 40% ammonium hydroxide. Collection of the ammonium hydroxide eluate gave a solution of the ammonium salt of 3 which upon lyophilization yielded pure (2R,3S)-2-hydroxy-3-amino-3-phenylpropionic acid (37, 0.51 g, 77%). m.p. 235° C., decomp. (literature: Deng et. al J. Org. Chem. 57, (1992), 4320: m.p. 238° C., decomp.); rotation after conversion to the hydrochloride salt is [a]\o(25,D)=–14.5° (c 0.37, MeOH; [a]\o(25,D) –15.1° c 0.365, MeOH). 1H NMR (400 MHz, D$_2$O) δ 4.09 (d, J=6.0 Hz, 1H), 4.32 (d, J=6.0 Hz, 1H), 7.21–7.41 (m, 5H); $^{13}$C NMR (100 MHz, D$_2$O/DMSO) d 177.7, 135.4, 130.9, 130.7, 128.9, 75.0, 59.0.

N-Benzoyl-(2R, 3S)-2-hydroxy-3-amino-3-phenylpropionic Acid (4); FIG. 3.

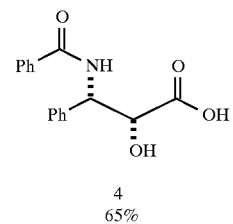

4
65%

Compound 4. The enantiomerically enriched 37 (0.43 g, 2.37 mmol) was converted to N-benzoyl-(2R,3S)-2-hydroxy-3-amino-3-phenylpropionic acid (4, 0.44 g, 65%) according to our earlier Schotten-Baumann-based procedure for this same transformation (Sharpless et al. J. Org. Chem. 59 (1994), 5104). Chemically and enantiomerically pure 4 was isolated by simple filtration of the solid which appeared when the pH of the reaction mixture was adjusted to ca. 2 by addition of aqueous HCl. m.p. 166°–167° C. (lit: Ojima et al. J. Org. Chem 56 (1991) 1681: 167°–169° C.); [a]\o(25,D) –34.0° (c 0.50, EtOH) (lit: Sharpless et al. J. Org. Chem. 1976, 41, 177: [a]\o(25,D) –35.9° c 0.565, EtOH); lit3d [a]\o(25,D) –35.5° (c 1.07, EtOH); 1H NMR (400 MHz, DMSO) δ 4.37 (d, J=4.3 Hz, 1H), 5.46 (dd, J=8.8, 4.2 Hz, 1H), 7.22–7.55 (m, 9H), 7.84 (d, J=7.2 Hz, 1H), 8.60 (d, J=8.9 Hz, 1H), 12.73 (br, 1H); $^{13}$C NMR (100 MHz, DMSO) δ 173.5, 166.0, 140.3, 134.4, 131.4, 128.4, 128.0, 127.4, 127.2, 126.9, 73.6, 55.8.

Figure 4:
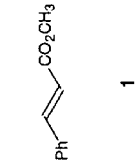
FIG. 4 tabulates a series of products formed from catalytic asymmetric aminohydroxylation in 1:1 $CH_3CN/H_2O$ (procedure 1). [a] All absolute configurations have been determined, see experimental procedure. [b] Numbers in parentheses are after recrystallizations from methanol (in some cases, it is the mother liquor which is enantioenriched when the racemate crystallizes preferentially—in the case of methylcinnamate only 2.5 mol % ligand and 2.0 mol % osmium catalyst were used, due to the preferential crystallization); the melting points and optical rotations (in 95% ethanol) are for the highest ee samples in the (DHQ)$_2$-PHAL column of Table 1. [c] The ee's in this column are for the products which are enantiomeric to those in the "Product" column. [d] 4:3 $CH_3CN/H_2O$ was used as the solvent.
Figure 5:
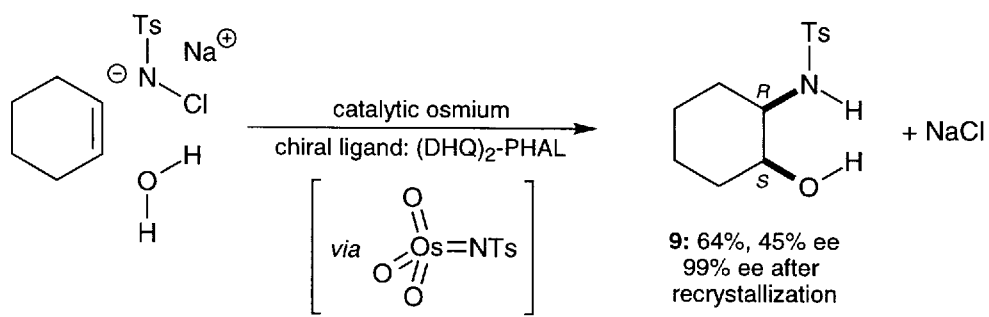
FIG. 5 illustrates a suggested mechanism and reactive species formed via the generation of the α-hydroxy-β-sulfonamide 9 from cyclohexene and $K_2OsO_2(OH)_4$, 4%; $(DHQ)_2$-PHAL or $(DHQD)_2$-PHAL, 5%; $TsNClNa.3H_2O$ and 1:1 solvent mix.

General procedure 1 (FIG. 4): Catalytic asymmetric aminohydroxylation in 1:1 acetonitrile/water (used for synthesis of compounds 2, 5, 6, 7, 8 or 9). To a stirred solution of (DHQ)$_2$-PHAL (0.11 g, 0.14 mmol, 5 mol %) in 20 mL of acetonitrile and 20 mL of water, in any convenient-sized glass vessel or vial, was added desired olefin (all commercially available from Aldrich, FIG. 4, 2.8 mmol), Chloramine-T trihydrate (2.42 g, 8.4 mmol, 3 eq) and K$_2$OsO$_2$(OH)$_4$ (41.6 mg, 0.112 mmol, 4 mol %). As the reaction proceeded to completion over the course of about one and half hours at room temperature, the color of the solution changed from yellow to pale green, then deep green and finally back to yellow (for entry 3 in Table 1, the yellow color remains throughout). After addition of aqueous sodium sulfite (1.0 g in 15 mL H$_2$O), the phases were separated, and the aqueous phase extracted with ethyl acetate (3×15 mL). The combined organic extracts were washed with brine, dried over MgSO$_4$ and the solvent concentrated to give the crude product, which also contains the p-toluenesulfonamide by-product produced upon the reduction of the excess Chloramine-T. In the case of the ethyl crotonate derivative, product 5, flash chromatography (6:4:1 hexane/CHCl3/MeOH) of this material provided 0.44 g (52% yield, 74% ee) of (2R,3S)-ethyl-N-(p-toluenesulfonyl)-2-hydroxy-3-amino-butanoate (5) as a clear oil eluting before the p-toluenesulfonamide impurity (52% yield, 74% ee). Similar purification provides compounds 2, 6, 7, 8 and 9. with the indicated yields and conditions shown in FIG. 4. NOTE: Replacement of the 3 eq of Chloramine-T with 1.5 eq of Chloramine-T and 1.5 eq of Et$_4$NOAc gives comparable results and reduces the amount of p-toluenesulfonamide by-product formed. This can greatly simplify product isolation, especially in cases where the product and the toluenesulfonamide have similar chromatographic mobilities.

General Procedure 2 (FIG. 6): Catalytic asymmetric aminohydroxylation in 1:1 tertbutanol/water (used for synthesis of compounds 2, 7 or 8). To a solution of (DHQ)2-PHAL (2.20 g, 2.80 mmol, 5 mol %) in t-BuOH (100 mL) and water (100 ml) in 500 mL Erlenmeyer or round-bottomed flask were added in order, desired olefin (56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 2.5 hr. Over the course of the reaction, the color changed from brown to deep green and then back to yellow as the stilbene slurry became a hydroxysulfonamide slurry. The product was isolated by filtration and the crude solid was washed once with cold (ca 5° C.) 1:1 t-BuOH/H$_2$O (15 mL) to yield the product hydroxysulfonamide. In the case of product 7, 16.1 g of N-(p-toluenesulfonyl)-(1S,2S)-2-amino-1,2-diphenylethanol (7) (78% yield, 64% ee, pure by NMR and HPLC). Trituration of this product twice with ethyl acetate(2×15 mL) at room temperature in a sintered glass funnel gave enantiomerically pure 7 (10.3 g, 50% yield, >99% ee, mp 166°–167° C.). See Sharpless, J. Org. Chem. 1994, 59, 5104 and Sharpless, J. Org. Chem. 1994, 59, 8302 for analogous solid-to-solid AD procedures.

Analysis of enantiomeric excesses for 2–9. Methyl cinnamate derivative 2: Chiralcel OG, 30% i-PrOH/hexane, 1 mL/min; 21.8 min (2S,3R), 28.3 min (2R,3S). Ethyl crotonate derivative 5: Chiralcel OD-H, 15% i-PrOH/hexane, 1 mL/min, 7.5 min (2S,3R), 13.4 min (2R,3S). Dimethyl fumarate derivative 6: Chiralcel OG, 30% i-PrOH/hexane, 1 mL/min, 16.7 min (2S,3S), 21.8 min (2R,3R). trans-Stilbene derivative 5: Chiralcel OD-H, 15% i-PrOH/hexane, 1 mL/min, 16.2 min (1S,2S), 26.0 min (1R,2R). cis-Stilbene derivative 8: Chiralcel OD-H, 15% i-PrOH/hexane, 0.5 mL/min, 18.5 min (1S,2R), 22.1 min (1R,2S). Cyclohexene derivative 9: Chiralcel OG, 15% i-PrOH/hexane, 0.5 mL/min, 28.5 min (1S,2R), 34.4 min (1R,2S).

Correlation of the absolute configurations of 2–9. Methyl cinnamate derivative (2R,3S)-2: Authentic (2R,3S)-2 was synthesized from N-benzoyl-(2R,3S)-3-phenylisoserine methyl ester (Taxol C-13 side chain; synthesis provided from Collet et al, Ecole normal superiure de Lyon, private communication) [6N HCl, reflux (remove methyl ester and N-benzoyl); SOCl$_2$, methanol (esterification); TsCl, K$_2$CO$_3$, 1:1 acetone/water (N-sulfonylation)] [HPLC: vide supra].

Ethyl crotonate derivative (2R, 3S)-5:

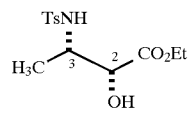

5

Compound 5: (2R,3S)-5 was converted to N-tosyl-(2S)-alanine methyl ester [6N HCl (hydrolysis); RuCl$_3$/H$_5$IO$_6$ (oxidative cleavage); SOCl$_2$, methanol (esterification)] [HPLC: Chiralcel OD-H, 15% i-PrOH/hexane, 1 mL/min, 16.1 min (2R), 17.0 min (2S)].

Dimethyl fumarate derivative (2R, 3R)-6:

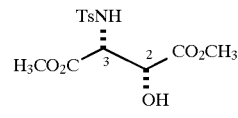

6

Compound 6: (2R,3R)-6 was converted to its N-tosyl-(2R,3R)-2-oxazolidinone derivative which was independently synthesized from (1S,2S)-7 [carbonyl diimidazole, CH$_2$Cl$_2$; RuCl$_3$, H$_5$IO$_6$ (oxidative degradation of the phenyl groups);(Polt et. al. J. Org. Chem. 1992, 57, 5469), SOCl$_2$, methanol (esterification)] [HPLC: Chiralcel OD-H, 15% i-PrOH/hexane, 1 mL/min, 26.0 min (1R,2R), 47.2 min (1S,2S)].

trans-Stilbene derivative (1S, 2S)-7:

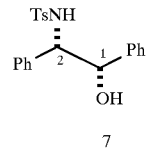

7

Compound 7: An authentic sample of (1S,2S)-7 was synthesized from (1R,2S)-8 [CrO$_3$, H$_2$SO$_4$ (alcohol to ketone); DIBAL-H reduction gave a 4:1 mixture of (1R,2S)-8 to (1S,2S)-7] [HPLC: vide supra].

cis-Stilbene derivative (1S, 2R)-8:

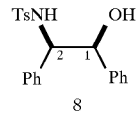

8

Compound 8: An authentic sample of (1R,2S)-8 was synthesized from (1R,2S)-2-amino-1,2-diphenylethanol [TsCl, K2CO3, acetone/water] [HPLC: vide supra].

Cyclohexene derivative (1S, 2R)-9:

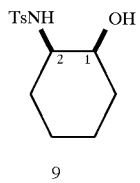

9

Compound 9: N,N'-ditosyl-(1R,2R)-diaminocyclohexane was synthesized from (1S,2R)-7 [SO$_2$Cl$_2$, Et$_3$N, EtOAc; NaH (cyclic sulfamidate formation); NaN$_3$ (opening); H$_2$, Pd/C (azide reduction); TsCl, K$_2$CO$_3$, 1:1 acetone/water] and compared to the compound derived from authentic (1R,2R)-diaminocyclohexane [22] [HPLC: Chiralcel AS, 20% i-PrOH/hexane, 1 mL/min, 23.2 min (1R,2R), 32.3 min (1S,2S)].

Figure 8:
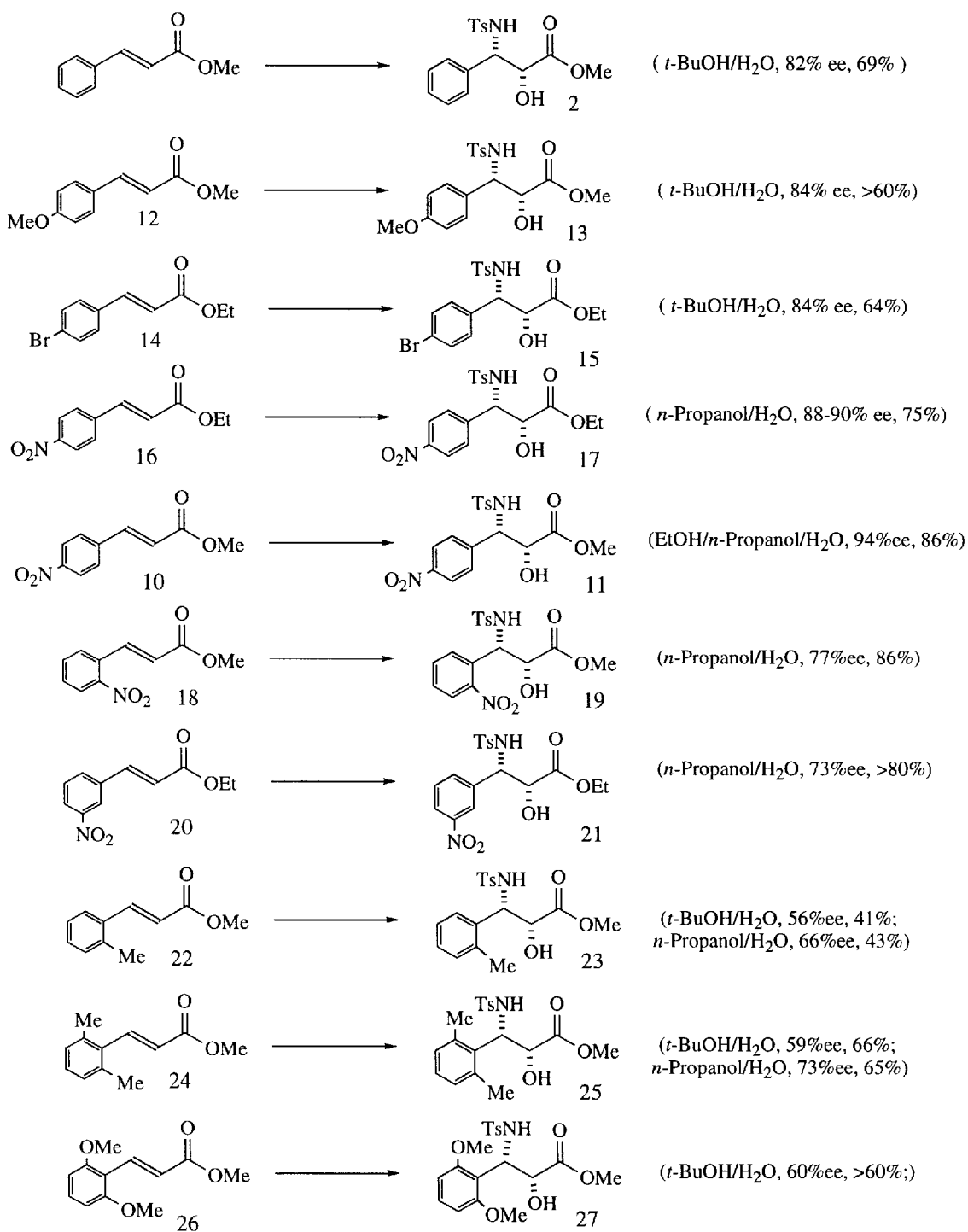
FIG. 8 shows a series of cinnamate derivatives which illustrate the effects of changing conditions. An electron withdrawing substituent on the phenyl ring of methylcinnamate as p-methoxy 12, p-bromo 14, p-nitro 16, p-nitro 10, o-nitro 18, m-nitro 20, o-methyl 22, 2,5 dimethyl 24, or 2,5 dimethyoxy 26, coupled with a solvent mix of $CH_3CN/H_2O$, n-propanol/$H_2O$, t-BuOH/$H_2O$, v/v=1:1 or (EtOH(5)/n-propanol(3)/$H_2O$ (5) provided the indicated enantiomeric excesses, regioselectivities and yields. The synthetic conditions were as follows: $K_2OsO_2(OH)_4$, 4%; $(DHQ)_2$-PHAL or $(DHQD)_2$-PHAL, 5%; $TsNClNa.3H_2O$, 3 eq.; indicated solvent mix; room temp., 3 h, 0.07M in olefin.

Catalytic Asymmetric Aminohydroxylation in 1:1 Tertbutanol/water (Used for Synthesis of Compounds 2, 13, 15, 23, 25 or 27) as Illustrated in FIG. 8

Compounds 2, 13, 15, 23, 25 or 27. To a solution of (DHQ)$_2$-PHAL (2.20 g, 2.80 mmol, 5 mol %) in t-BuOH (100 mL) and water (100 ml) in 500 mL Erlenmeyer or round-bottomed flask were added in order, desired olefin (methyl cinnamate, p-methoxy-methyl-cinnamate 12, p-bromo-ethyl-cinnamate 14, o-methyl-methyl-cinnamate 22, 2,5-dimethyl-methyl-cinnamate 24 or 2,5-dimethoxy-methyl-cinnamate 26; all commercially available from Aldrich) (56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 2.5 hr. Over the course of the reaction, the color changed from brown to deep green and then back to yellow as the stilbene slurry became a hydroxysulfonamide slurry. The product was isolated by filtration and the crude solid was washed once with cold (ca 5° C.) 1:1 t-BuOH/H$_2$O (15 mL) to yield the product β-hydroxysulfonamide. Trituration of this product twice with ethyl acetate (2×15 mL) at room temperature in a sintered glass funnel gave enantiomerically pure β-hydroxysulfonamide compounds 2, 13, 15, 23, 25 or 27.

Figure 7:
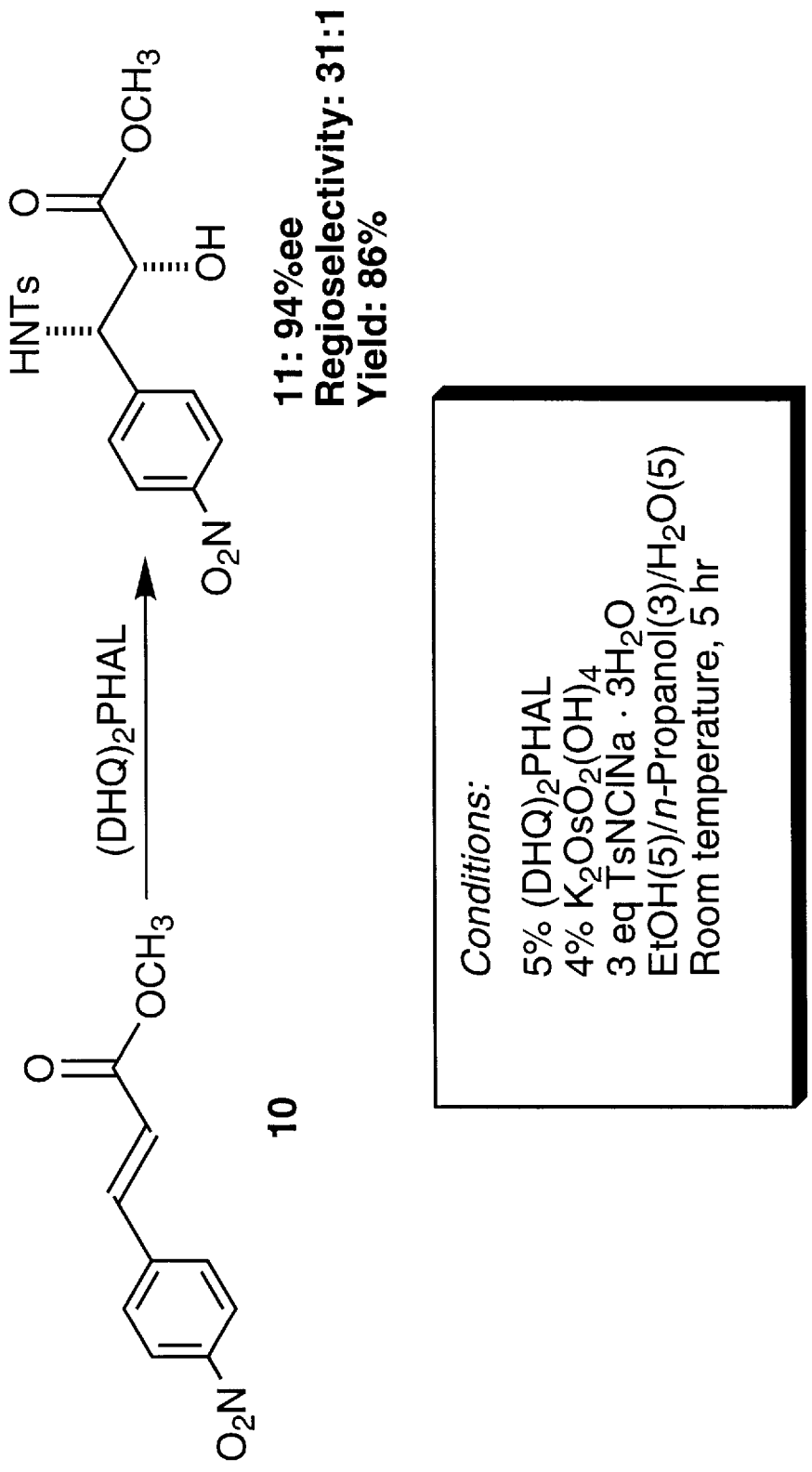
FIG. 7 illustrates the effects of changing conditions on the synthesis of α-hydroxy-β-sulfonamide compound 11. An electron withdrawing substituent on the phenyl ring of methylcinnamate via p-nitro-methylcinnamate, coupled with a 3 solvent mix (EtOH(5)/n-propanol(3)/$H_2O$ (5) and 5 hour reaction time, increases enantiomeric excess to 94%, regioselectivity to 31:1 and yield to 86%. The synthetic conditions are as follows: $K_2OsO_2(OH)_4$, 4%; $(DHQ)_2$-PHAL or $(DHQD)_2$-PHAL, 5%; $TsNClNa.3H_2O$, 3 eq.; (EtOH(5)/n-propanol(3)/$H_2O$ (5); Room temp., 5 h, 0.07M in olefin.

Catalytic asymmetric aminohydroxylation in 1:1:1 ethanol/n-propanol/water (used for synthesis of compound 11) as illustrated in FIGS. 7 and 8.

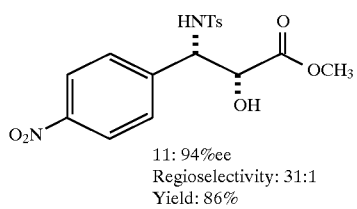

11: 94%ee
Regioselectivity: 31:1
Yield: 86%

To a solution of (DHQ)$_2$-PHAL (2.20 g, 2.80 mmol, 5 mol %) in ethanol (63 mL) n-Propanol (63 mL) and water (63 ml) in 500 mL Erlenmeyer or round-bottomed flask were added in order, commercially available p-nitro methyl cinnamate derivative (10; Aldrich chemical company) (9.08 g, 56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 5 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/H$_2$O (15 mL) to yield enantiomerically pure β-hydroxysulfonamide compound 11 in 86% overall yield and 94% ee.

Catalytic Asymmetric Aminohydroxylation in 1:1 n-Propanol/water (Used for Synthesis of Compounds 17, 19, 21, 23 or 25) as Illustrated in FIG. 8

Compounds 17, 19, 21, 23 or 25. To a solution of (DHQ)$_2$-PHAL (2.20 g, 2.80 mmol, 5 mol %) in n-Propanol (100 mL) and water (100 ml) in 500 mL Erlenmeyer or round-bottomed flask were added in order, commercially available methyl or ethyl cinnamate derivatives (16, 18, 20, 22 or 24; Aldrich chemical company) (9.08 g, 56.0 mmol), Chloramine-T trihydrate (48.4 g, 0.168 mol, 3.0 eq) and K$_2$OsO$_2$(OH)$_4$ (0.824 g, 2.24 mmol, 4 mol %). The reaction flask was immersed in a room-temperature water bath and the slurry stirred for 3 hr. Over the course of the reaction, the color changed from brown to deep green and then back to yellow as hydroxysulfonamide product appeared as white precipitates. The flask was then immersed in an ice bath (0° C.) for 20 min. During this cooling, almost all of crystalline hydroxysulfonamide product precipitated from the reaction solution. The product was isolated by filtration and the crude solid was washed once with cold (ca 5° C.) 1:1 n-Propanol/H$_2$O (15 mL) to yield enantiomerically pure β-hydroxysulfonamide compounds 17, 19, 21, 23 or 25.

Preparation of sulfonamides form sulfonychlorides (as illustrated in FIGS. 9 and 13)

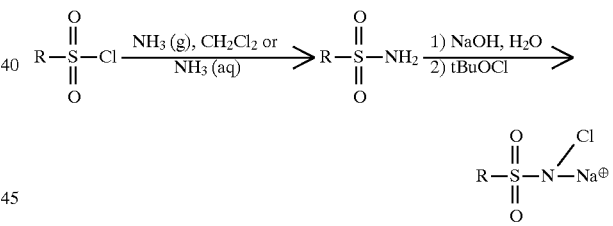

The sulfonyl chlorides used in the formation of the sulfonamides can come from commercially available sources such as Aldrich, Fluka, Sigma etc., or can be prepared from a procedure developed by Campbell et al. Chem Rev. 1978, 78, 65, for the preparation of N-chloro-N-sodiocarbamates which is a general procedure in the synthesis of N-chloro-N-sodio-aryl-and alkylsulfonamides. The sulfonyl chlorides (R-SO$_2$Cl) formed can include compounds where R=4-Me-Ph-, 4-MeOPh, Me, Ph-CH2-, 4-NO2-Ph-, 2-NO2-Ph-, 2-Naphthyl,1-Napthyl, Dansyl (FIGS. 9 and 12) or derivatives selected from the following functional groups: acyclic or cyclic hydrocarbons, hydroxyl compounds, ethers, protected amines, carbonyl compounds, esters or carboxylic acids, n-alkyl, alkynes (60) pyrans, pyrroles (54), various heterocycles including: nitriles (58), pyrazines, pyrazoles (55), pyridazines, pyridines (57), pyrimidines (59), pyrrolizines, quinazolines, quionlines, thiophenes, silanes, CHnX where X=OR$_1$, halogens, aromatic rings, heterocycles, silyl groups and n=1 to 2 (56) (FIG. 13).

Method A: Using a Sulfonyl Chloride (as Obtained Supra) and Gaseous $NH_{3(g)}$ (FIG. 9)

$NH_3$ was bubbled (fritte or pipette) through well stirred $CH_2Cl_2$ (ca 100 ml) at RT. The sulfonyl chloride (100 mmol) was added in portions. After all of the sulfonyl chloride was added, stirring at RT under NH— was continued until TLC [hexane/ethylacetate] showed full conversion of the starting material. Precipitated NH4Cl was filtered off, the solvent was evaporated ($NH_3$) and the residue was crystallized from hot acetone/water and dried at high vaccum (oil pump, 0.1–0.01 torr) overnight to yield the crystalline, pure sulfonamides in nearly quantitative yields.

Method B: Using a Sulfonyl Chloride (as Obtained Supra) and Aqueous Ammonia (FIG. 9)

The sulfonylchloride (100 mmol) was added portionwise to a well stirred aqueous solution (100 ml) of NH3 (29.7%. Fisher) at RT. After all of the sulfonyl chloride was added, stirring at RT was continued for 2 more hours. The reaction mixture was slowly ($NH_3$!) heated to reflux and then cooled down to ca 4 C. The precipitated product was filtered off and crystallized from hot acetone/water and dried at high vaccum (oil pump, 0.1–0.01 torr) overnight to yield the crystalline, pure sulfonamides in nearly quantitative yields.

Trimethylsilylethyl sulfonamide and related akylsilyl-sulfonamides can be prepared according to a literature procedure: Steven M. Weinreb et al. Tetrahedron Lett. 1986, 27, 2099–2102.

General catalytic asymmetric aminodroxylation by in situ generation of chloramines different from Chloramine T (in situ generation of $R-SO_2NClNa$) as illustrated in FIG. 10.

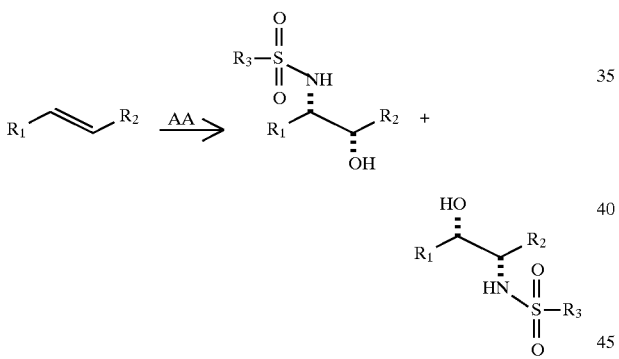

General procedure: T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to a solution of 40 mg (0.05 mmol, 0.05 eq) of $(DHQ)_2Phal$ or $(DHQD)_2Phal$ in 7.5 ml of MeCN (alternatively, a 1:1 mix of t-BuOH/water, n-propanol/water or 1:1:1 ethanol/n-proanol/water can be used, depending upon optimization conditions). Subsequently 190 mg (1.0 mmol, 1.0 eq) of olefin where $R_1$=acyclic or cyclic hydrocarbons, heterocycles, hydroxyl compounds, ethers, protected amines, sulfides, carbonyl compounds, acrylates, substituted acrylates, esters or carboxylic acids.

$R_2$=combination of $R_1$ $R_3$=4-Me-Ph-, 4-MeOPh, Me, Ph-CH2- , 4-NO2-Ph-, 2-NO2-Ph-, 2-Naphthyl,1-Napthyl, Dansyl or derivatives selected from the following functional groups: acyclic or cyclic hydrocarbons, hydroxyl compounds, ethers, protected amines, carbonyl compounds, esters or carboxylic acids, n-alkyl, pyrans, pyrroles, various heterocycles including: pyrazines, pyrazoles, pyridazines, pyridines, pyrimidines, pyrrolizines, quinazolines, quionlines, thiophenes, silanes, CHnX where X=$OR_1$, halogens, aromatic rings, heterocycles, silyl groups and n=1 to 2 (reagents commercially or synthetically available) and 14.7 mg (0.04 mmol, 0.04 eq) of $K_2OsO_2(OH)_4$ were added and the reaction mixture stirred at RT. After ca. 10 min all of the $K_2OsO_2(OH)_4$ was dissolved and the color of the reaction mixture turned to green. Stirring was continued until the green color of the reaction mixture had turned to yellow. 10 ml of aqueous $Na_2SO_3$ (sat.) were added to reduce excess Chloramine. The aqueous phase was seperated and extracted three times with ca. 30 ml ethyl acetate. The combined organic phases were washed with brine containing 1% of NaOH, dried over $MgSO_4$ (anhydrous) and the solvent was evaporated in vaccu. The residue was purified by flash chromatography ($SiO_2$, hexane/ethyl acetate) to afford the pure crystalline aminohydroxylation product. In cases where regioisomeric products could be formed yields refer to a mixture of the two regioisomeres. Crystallization from ethyl acetate/ hexane furnished the enantiomerically pure (>99% ee) N-aryl/alkylsulfonyl protected amino alcohol (FIG. 10)

Catalytic asymmetric aminohydroxylation of compounds 28–47 by in situ generation of chloramines different from Chloramine T (1 mmol scale, in situ generation of $R-SO_2NClNa$) as illustrated in FIG. 11 and tabulated in FIG. 12.

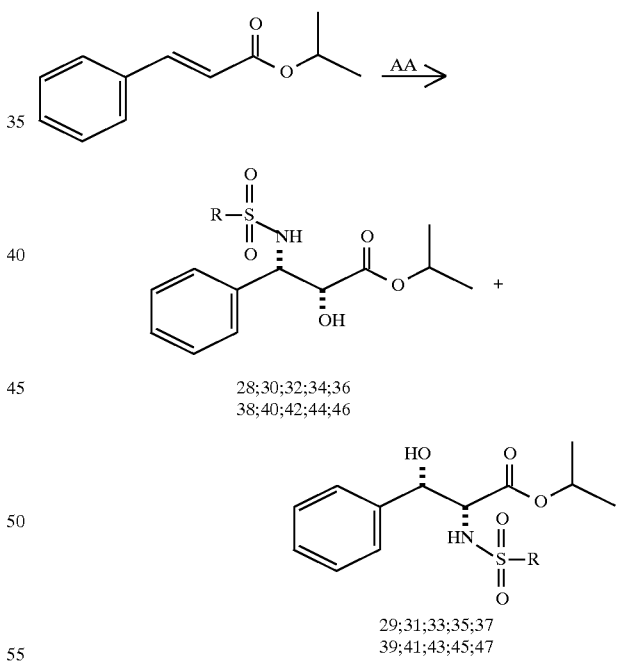

28;30;32;34;36
38;40;42;44;46

29;31;33;35;37
39;41;43;45;47

General procedure: T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to a solution of 40 mg (0.05 mmol, 0.05 eq) of $(DHQ)_2Phal$ or $(DHQD)_2Phal$ in 7.5 ml of MeCN (alternatively, a 1:1 mix of t-BuOH/water, n-propanol/water or 1:1:1 ethanol/n-proanol/water can be used, depending upon optimization conditions). Subsequently 190 mg (1.0 mmol, 1.0 eq) of isopropyl cinnamate (commercially available from Aldrich) and 14.7 mg (0.04 mmol, 0.04 eq) of K$_2$OsO$_2$(OH)$_4$ were added and the reaction mixture stirred at RT. After ca. 10 min all of the K$_2$OsO$_2$(OH)$_4$ was dissolved and the color of the reaction mixture turned to green. Stirring was continued until the green color of the reaction mixture had turned to yellow.

10 ml of aqueous Na$_2$SO$_3$ (sat.) were added to reduce excess Chloramine. The aqueous phase was seperated and extracted three times with ca. 30 ml ethyl acetate. The combined organic phases were washed with brine containing 1% of NaOH, dried over MgSO$_4$ (anhydrous) and the solvent was evaporated in vaccu. The residue was purified by flash chromatography (SiO$_2$, hexane/ethyl acetate) to afford the pure crystalline aminohydroxylation product. In cases where regioisomeric products could be formed yields refer to a mixture of the two regioisomeres. Crystallization from ethyl acetate/ hexane furnished the enantiomerically pure (>99% ee) N-aryl/alkylsulfonyl protected amino alcohol.

Preparation of the Chloramine M: 48 (CH$_3$SO$_2$NCl)

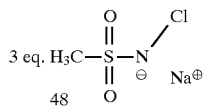

Chloramine M can be synthesized readily from methanesulfonamide (Aldrich chemical company) by addition of the stoichiometric amount of sodium hydroxide and t-butylhypochlorite in water or methanol. This method was adapted from a procedure developed by Campbell et al. Chem Rev. 1978, 78, 65, for the preparation of N-chloro-N-sodiocarbamates and proved to be general in the synthesis of N-chloro-N-sodio-aryl- and alkylsulfonamides. Chloramine M can be isolated either as a stable salt or can be prepared in situ, preferable in large scale syntheses.

Synthesis of chloramine M: To an ice-cold stirred solution of 4.81 g (50 mmol) of methanesulfonamide and 2.0 g (50 mmol) sodium hydroxide in 40 mL of dry methanol is added very slowly 5.63 mL (5.4 g, 50 mmol) t-butylhypochlorite. The solution is stirred for 1 h and dried in vacuo to afford the pure N-chloro,N-sodiomethanesulfonamide in quantitative yield (7.58 g).

CH$_3$NSO$_2$NaCl, MW: 151.54; Elementary analysis: calcd.: C 7.93, H 2.00, N 9.24, Na 15.17, Cl 23.39 found: C 8.03, H 2.08, N 9.24, Na 15.36, Cl 23.12

For the in situ generation of Chloramine M the preparation can be done in the sufficient amount of water required for the AA reaction by using the same protocol.

General Procedure for Synthesis of Hydroxysufonamides Using Chloramine M (MeSO$_2$NClNa) on a 1 mmol Scale (as Illustrated in FIG. 14 and Tabulated in FIG. 15)

To a well stirred solution of 40 mg of (DHQD)$_2$PHAL (0.05 mmol, 0.05 eq) in 7.5 ml of n-propanol (alternatively, a 1:1 mix of t-BuOH/water, acetonitrile/water or 1:1:1 ethanol/n-proanol/water can be used, depending upon optimization conditions) was slowly added a solution of 455 mg (3.0 mmol, 3.0 eq) of MeSO$_2$NClNa in 7.5 ml of water, which resulted in a clear colorless solution. The substrate olefin (all commercially available from Aldrich, FIG. 15, 1.0 mmol, 1.0 eq) and K$_2$OsO$_2$(OH)$_4$ (0.04 mmol, 0.04 eq) were subsequently added. Usually the reaction mixture turned green after some minutes and was stirred until color change to dark blue occured (3–16 h), however colour changes are not generally observed. 10 ml of aqueous Na2SO3 (sat.) were added to reduce the excess MeSO2NClNa. The aqueous phase was seperated and extracted three times with ca. 30 ml ethyl acetate. The combined organic phases were dried over MgSO4 (anhydrous) and the solvent was evaporated in vacuo.

To determine the exact yield the residue was purified by flash chromatography (SiO2, hexane/ethyl acetate) to afford the pure crystalline aminohydroxylation product. In cases where regioisomeric products can be formed yields refere to a mixture of the two regioisomeres. Crystallization from ethyl acetate/ hexane furnished the enantiomerically pure (>99% ee) methane sulfonyl protected amino alcohol.

For preparative purposes work-up and purification can be simplified. As the methanesulfonamide is insoluble in CH2Cl2 and ether, but good soluble in aqueous solution (even in saturated aqueous NaCl solution) it can be removed extractively. It can also be crystallized out in CH$_2$Cl$_2$ or CH$_2$Cl$_2$/hexane mixtures. Alternatively it can be sublimed from the crude material at 80° C. Crystallization from ethyl acetate/ hexane could usually furnish the chemically and enantiomerically pure (>99% ee) methane sulfonyl protected amino alcohol.

Asymmetric aminohydroxylation in 1:1 acetonitrile/water (used for synthesis of acrylates and methacrylates as shown in FIGS. 16 and 17).

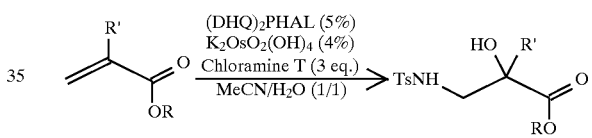

To a stirred solution of (DHQ)$_2$-PHAL (0.11 g, 0.14 mmol, 5 mol %) in 20 mL of acetonitrile and 20 mL of water, in any convenient-sized glass vessel or vial, was added desired acrylate or methacrylates entries 1–10 (all commercially available from Aldrich, FIG. 16 and FIG. 17, 2.8 mmol), Chloramine-T trihydrate (2.42 g, 8.4 mmol, 3 eq) and K$_2$OsO$_2$(OH)$_4$ (41.6 mg, 0.112 mmol, 4 mol %). As the reaction proceeded to completion over the course of about one and half hours at room temperature, the color of the solution changed from yellow to pale green, then deep green and finally back to yellow. After addition of aqueous sodium sulfite (1.0 g in 15 mL H$_2$O), the phases were separated, and the aqueous phase extracted with ethyl acetate (3×15 mL). The combined organic extracts were washed with brine, dried over MgSO$_4$ and the solvent concentrated to give the crude product, which also contains the p-toluenesulfonamide by-product produced upon the reduction of the excess Chloramine-T. Purification provides compounds as shown in FIG. 16, entries 1–10 with the indicated yields and conditions. NOTE: Replacement of the 3 eq of Chloramine-T with 1.5 eq of Chloramine-T and 1.5 eq of Et$_4$NOAc gives comparable results and reduces the amount of p-toluenesulfonamide by-product formed. This can greatly simplify product isolation, especially in cases where the product and the toluenesulfonamide have similar chromatographic mobilities.

General procedure for synthesis of compound 2 (FIG.18):

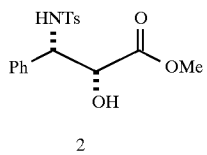

2

Compound 2: T-butyl hypochlorite was slowly added to a well stirred solution of the desired sulfonamide (as obtained vida supra; 3.1 mmol, 3.1 eq) and 122 mg (3.05 mmol. 3.05 eq) of NaOH in 7.5 ml of water at room temperature. After 10 more minutes of stirring this solution was added dropwise to a solution of 40 mg (0.05 mmol, 0.05 eq) of $(DHQ)_2Phal$ or $(DHQD)_2Phal$ in 7.5 ml of MeCN (alternatively, a 1:1 mix of t-BuOH/water, n-propanol/water or 1:1:1 ethanol/n-proanol/water can be used, depending upon optimization conditions). Subsequently 190 mg (1.0 mmol, 1.0 eq) of methyl cinnamate (commercially available from Aldrich) and 14.7 mg (0.04 mmol, 0.04 eq) of $K_2OsO_2(OH)_4$ were added and the reaction mixture stirred at RT. After ca. 10 min all of the $K_2OsO_2(OH)_4$ was dissolved and the color of the reaction mixture turned to green. Stirring was continued until the green color of the reaction mixture had turned to yellow.

10 ml of aqueous $Na_2SO_3$ (sat.) were added to reduce excess Chloramine. The aqueous phase was seperated and extracted three times with ca. 30 ml ethyl acetate. The combined organic phases were washed with brine containing 1% of NaOH, dried over $MgSO_4$ (anhydrous) and the solvent was evaporated in vaccu. The residue was purified by flash chromatography ($SiO_2$, hexane/ethyl acetate) to afford the pure crystalline aminohydroxylation product. In cases where regioisomeric products could be formed yields refer to a mixture of the two regioisomeres. Crystallization from ethyl acetate/ hexane furnished the enantiomerically pure (>99% ee) N-aryl/alkylsulfonyl protected amino alcohol.

Synthesis of β-hydroxy-α-N-aryl/alkylsulfonyl protected aminoacids 62 or 63 via aziridine intermediate 61 (FIG.18):

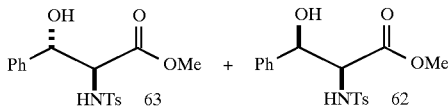

Compounds 62 and 63: To the AA product 2 (2.15 mmol), in a THF solution (0.10M), was added $P(Ph)_3$ (1.1 equivalents triphenylphosphine) and diethyl azodicarboxylate (1.1 equivalents, all commercially available from Aldrich). The mixture was next stirred at room temperature for 1 hour and then worked up according to the procedure of Mitsunobu et al. *Tetrahedron Letters,* 1989, 5709. The resulting arizidine (0.302 mmol) was dissolved in a 6:4 v/v mixture of 1,4-dioxane/$H_2O$ and 0.03 mL of TFA (trifluroacetic acid) was added as the catalyst. The reaction was then run at 100° C. for 24° C. The mixture was diluted with ethylacetate and separated from the aqueous phase. The aqueous phase was seperated and extracted three times with ca. 30 ml ethyl acetate. The combined organic phases were washed with brine containing 1% of NaOH, dried over $MgSO_4$ (anhydrous) and the solvent was evaporated in vacuo. The residue was purified by flash chromatography ($SiO_2$, hexane/ethyl acetate) to afford the pure crystalline aminohydroxylation product. In case where regioisomeric products are formed, crystallization from ethyl acetate/hexane furnishes the enantiomerically pure (>99% ee) β-hydroxy-α-N-aryl/alkylsulfonyl protected aminoacid 62 or 63.

What is claimed is:

1. An improved method for converting an olefinic substrate to an asymmetric hydroxylamine product by asymmetric addition of a nitrogen source and a hydroxyl radical to the olefinic substrate, the method being of a type which employs a reaction solution which includes osmium as a catalyst, a chiral ligand for enantiomerically directing said asymmetric addition, the olefinic substrate being present and soluble at a stoichiometric concentration within the reaction solution, the osmium bing present and soluble within the reaction solution at a catalytic concentration, wherein the improvement comprises the following substeps:

Substep A: said asymmetric addition is performed using a sulfonamide as the nitrogen source for forming an asymmetric hydroxysulfonamide intermediate; and then:

Substep B: said conversion is completed by deprotecting the asymmetric hydroxysulfonamide intermediate in said Substep A for forming the asymmetric hydroxylamine product.

2. A method for converting an olefinic substrate to an asymmetric hydroxysulfonamide product comprising the step of:

catalyzing an asymmetric addition to the olefinic substrate of a sulfonamidyl radical and a hydroxyl radical by means of an osmium catalyst, said catalysis occurring in the presence of a chiral ligand for enantiomerically directing the asymmetric addition.

3. A method for converting an olefinic substrate to an asymmetric hydroxysulfonamide product as described in claim 2 wherein the sulfonamide is a chloramine compound.

4. A method for converting an olefinic substrate to an asymmetric hydroxysulfonamide product as described in claim 2 wherein said asymmetric addition occurs in a co-solvent mixture containing an organic component and an aqueous component.

5. A method for converting an olefinic substrate to an asymmetric hydroxysulfonamide product as described in claim 4 wherein the organic component of the solvent is selected from the group consisting of acetonitrile, tert-butanol, and n-propanol.

6. A method for converting an olefinic substrate to an asymmetric hydroxysulfonamide product as described in claim 4 wherein the aqueous and organic components of the co-solvent are each approximately 50% on a volume basis.

7. A method for converting an olefinic substrate to an asymmetric hydroxysulfonamide product as described in claim 2 wherein said catalysis occurs substantially in the absence of an ancillary metal salt.

8. A method for converting an olefinic substrate to an asymmetric hydroxysulfonamide product as described in claim 7 wherein the ancillary metal salt is selected from the group consisting of silver salts and mercury salts.

* * * * *

UNITED STATES PATENT AND TRADEMARK OFFICE
CERTIFICATE OF CORRECTION

PATENT NO. : 5,859,281
DATED : January 12, 1999
INVENTOR(S) : Sharpless, et al.

It is certified that error appears in the above-identified patent and that said Letters Patent is hereby corrected as shown below:

In Column 1, line 4, insert:

--This invention was made with government support under Contract No. HL14197 by the National Institutes of Health and Contract No. CHE-9296055 by the National Science Founcation. The government has certain rights in the invention.--

Signed and Sealed this

Seventeenth Day of August, 1999

Attest:

Q. TODD DICKINSON

Attesting Officer

Acting Commissioner of Patents and Trademarks